US005807745A

United States Patent [19]

Furie et al.

[11] Patent Number: 5,807,745
[45] Date of Patent: Sep. 15, 1998

[54] METHOD OF INHIBITING PADGEM-MEDIATED OR ELAM-1-MEDIATED LEUKOCYTE ADHESION USING AN INHIBITOR COMPRISING A LE$^x$ CORE COMPONENT

[75] Inventors: Bruce Furie; Barbara C. Furie, both of Wellesley, Mass.; Eric Larsen, Lebanon, N.H.; Theresa Palabrica, Quincy, Mass.; Susan A. Sajer, Brookline, Mass.; Denisa D. Wagner, Wellesley, Mass.

[73] Assignee: New England Medical Center Hospitals, Inc., Boston, Mass.

[21] Appl. No.: 379,080

[22] Filed: Jan. 26, 1995

Related U.S. Application Data

[63] Continuation of Ser. No. 230,862, Apr. 19, 1994, abandoned, which is a continuation of Ser. No. 667,030, Mar. 11, 1991, abandoned.

[51] Int. Cl.$^6$ .................................. C12N 5/00; C12N 5/06
[52] U.S. Cl. ............................ 435/375; 436/63; 436/501
[58] Field of Search ............................... 424/130.1, 137.1; 514/8, 23, 21; 435/375; 436/501

[56] References Cited

U.S. PATENT DOCUMENTS

| | | | |
|---|---|---|---|
| 3,928,587 | 12/1975 | Sawyer | 424/230 |
| 4,344,936 | 8/1982 | Soslau | 424/101 |
| 4,783,330 | 11/1988 | Furie et al. | 424/1.1 |
| 4,820,505 | 4/1989 | Ginsberg et al. | 424/9 |
| 5,045,453 | 9/1991 | Katapodis | 435/18 |
| 5,143,712 | 9/1992 | Brandley et al. | 424/1.1 |
| 5,198,424 | 3/1993 | McEver | 514/13 |
| 5,211,936 | 5/1993 | Brandley et al. | 424/1.12 |
| 5,378,464 | 1/1995 | McEver | 424/143.1 |
| 5,428,025 | 6/1995 | Brandley et al. | 514/55 |
| 5,464,778 | 11/1995 | Cummings et al. | 436/503 |
| 5,470,842 | 11/1995 | Brandley et al. | 514/61 |

FOREIGN PATENT DOCUMENTS

| | | |
|---|---|---|
| WO 90/13300 | 11/1990 | WIPO . |
| WO 91/06632 | 5/1991 | WIPO . |
| WO 91/16900 | 11/1991 | WIPO . |
| WO 91/19501 | 12/1991 | WIPO . |
| WO 91/19502 | 12/1991 | WIPO . |
| WO 92/01718 | 2/1992 | WIPO . |
| WO 92/02527 | 2/1992 | WIPO . |
| WO 92/07572 | 5/1992 | WIPO . |
| WO 92/09293 | 6/1992 | WIPO . |

OTHER PUBLICATIONS

Corral, L., et al., "Requirement for Sialic Acid on Neutrophils in a GMP–140 (PADGEM) Mediated Adhesive Interaction With Activated Platelets," *Biochem. Biophys. Res. Comm.*, 172(3):1349–1356 (1990).
Moore, K.L., et al., "GMP–140 Binds to a Glycoprotein Receptor on Human Neutrophils: Evidence for a Lectin-–Like Interaction," *J. Cell Biol.*, 112(3):491–499 (1991).
Johnston, G.I., et al., "Cloning of GMP–140, a Granule Membrane Protein of Platelets and Endothelium: Sequence Similarity to Proteins Involved in Cell Adhesion and Inflammation," *Cell*, 56:1033–1044 (1989).
Skinner, M.P., et al., "Characterization of Human Platelet GMP–140 as a Heparin–Binding Protein," *Biochem. Biophys. Res. Commun.*, 163(3):1373–1379 (1989).
Larsen, E., et al., "PADGEM Protein: A Receptor That Mediates the Interaction of Activated Platelets with Neutrophils and Monocytes," *Cell*, 59:305–312 (1989).
Hamburger, S.A. and McEver, R.P., "GMP–140 Mediates Adhesion of Stimulated Platelets to Neutrophils," *Blood*, 75(3):550–554 (1990).
Geng, J–G., et al., "Rapid Neutrophil Adhesion to Activated Endothelium Mediated by GMP–140," *Nature*, 343:757–760 (1990).
Larsen, E., et al., "PADGEM–Dependent Adhesion of Platelets to Monocytes and Neutrophils is Mediated by Lineage–Specific Carbohydrate, LNF III (CD15)," *Cell*, 63:467–474 (1990).
Marx, J.L., "New Family of Adhesion Proteins Discovered," *Science*, 234:1144 (1989).
Ohmori, K., et al., "Sialyl SSEA–1 Antigen as a Carbohydrate Marker of Human Natural Killer Cells and Immature Lympnoid Cells," *Blood*, 74(1):255–261 (1989).
Parmentier, S., et al., "New Families of Adhesion Molecules Play a Vital Role in Platelet Functions," *Immunol. Today*, 11(7):225–227 (1990).
Springer, T.A. and Lasky, L.A., "Sticky Sugars for Selections," *Nature*, 349:196–197 (1991).
Brandley, B.K., et al., "Carbohydrates Ligands of the LEC Cell Adhesion Molecules," *Cell*, 63:861–863 (1990).
Osborn, L., "Leukocyte Adhesion to Endothelium in Inflammation," *Cell*, 62:3–6 (1990).
Stoolman, L.M., "Adhesion Molecules Controlling Lymphocyte Migration," *Cell*, 56:907–910 (1989).
Tiemeyer, M., et al., "Identification and Structural Determination of an Endogenous Carbohydrate Ligand for ELAM–1," *J. Cell. Biol.*, 111(5) (part 2): 159a, abstract No. 871 (1990).

(List continued on next page.)

*Primary Examiner*—Lila Feisee
*Assistant Examiner*—Phillip Gambel
*Attorney, Agent, or Firm*—Hamilton, Brook, Smith & Reynolds, P.C.

[57] ABSTRACT

The present invention relates to a method of inhibiting (reducing or preventing) the interaction of a cell which bears a surface molecule that interacts with a ligand comprising a Le$^x$ core with its target ligand by contacting the cell with an inhibitor comprising a Lewis x (Le$^x$) core. The invention further relates to a method of inhibiting (reducing or preventing) the interaction or adhesion of endothelial cells and/or platelets with leukocytes (i.e., white blood cells), especially with nonlymphocytic leukocytes such as neutrophils and monocytes, by contacting the endothelial cells and/or platelets with an inhibitor comprising a Le$^x$ core under conditions whereby adhesion is inhibited.

17 Claims, 7 Drawing Sheets

OTHER PUBLICATIONS

Tiemeyer, M., et al., "Carbohydrate Ligand for Endothelial–Leukocyte Adhesion Molecule 1," *Proc. Natl. Acad. Sci. USA,* 88:1138–1142 (1991).

Walz, G., et al., "Recognition by ELAM–1 of the Sialyl–Le$^x$ Determinant on Myeloid and Tumor Cells," *Science,* 250:1132–1135 (1990).

Phillips, M.L., et al., "ELAM–1 Mediates Cell Adhesion by Recognition of a Carbohydrate Ligand, Sialyl–Le$^x$," *Science,* 250:1130–1132 (1992).

Lowe, J.B., et al., "ELAM–1–Dependent Cell Adhesion to Vascular Endothelium Determined by a Transfected Human Fucosyltransferase cDNA," *Cell,* 63:475–484 (1990).

Goelz, S.E., et al., "ELFT: A Gene That Directs the Expression of an ELAM–1 Ligand," *Cell,* 63:1349–1356 (1990).

Rice, G.E. and Bevilacqua, M.P., "An Inducible Endothelial Cell Surface Glycoprotein Mediates Melanoma Adhesion," *Science,* 246:1303–1306 (1989).

Hession, C., et al., "Endothelial Leukocyte Adhesion Molecule 1: Direct Expression Cloning and Functional Interactions," *Proc. Natl. Acad. Sci. USA,* 87:1673–1677 (1990).

Shimizu, Y., et al., "Activation–Independent Binding of Human Memory T Cells to Adhesion Molecule ELAM–1," *Nature,* 349:799–802 (1991).

Sherman–Gold, R., *Genentech's Deal with Glycomed Illustrates Industry's Rising Interest in Glycobiology,* Genetic Engineering New, Feb., 1991, at 1, col. 3.

Zhou, Q., et al., "The Selection GMP–140 Binds to Sialylated, Fucosylated Lactosaminoglycans on Both Myeloid and Nonmyeloid Cells," *J. Cell. Biol.,* 115(2):557–564 (1991).

Polley, M.J., et al., "CD62 and Endothelial Cell–Leukocyte Adhesion Molecule 1 (ELAM–1) Recognize the Same Carbohydrate Ligand, Sialyl–Lews x," *Proc. Natl. Acad. Sci. USA,* 88:6224–6228 (1991).

Celi, A., et al., "PADGEM: An Adhesion Receptor for Leukocytes on Stimulated Platelets and Endothelial Cells (43309A)," *Proc. Soc. Exp. Med.,* 198(2):703–709 (1991).

Moore, K.L. and R.P. McEver, "Analysis of Granule Membrane Protein–140 Binding to its Putative Neutrophil Receptor", *Clinical Research,* 38(2):364A (1990).

Kieffer, N. and D.R. Phillips, "Platelet Membrane Glycoproteins: Functions in Cellular Interactions", *Annu. Rev. Cell Biol.,* 6:329–57 (1990).

Parmentier, S., et al., "Inhibition of Platelet Functions by a Monoclonal Antibody (LYP20) Directed Against a Granule Membrane Glycoprotein (GMP–140/PADGEM)", *Blood,* 77(8):1734–1739 (1991).

Fukuda, M., et al., "Structure of Sialylated Fucosyl Lactosaminoglycan Isolated from Human Granulocytes", *Journal of Biological Chemistry,* 259(17):10925–10935 (1984).

Mulligan, M.S., et al., "Protective effects of oligosaccharides in P–selectin–dependent lung injury", *Nature,* 364:149–151 (1993).

Palabrica, T., et al., "Leukocyte accumulation promoting fibrin deposition is mediated in vivo by P–selectin on adherent platelets", *Nature,* 359:848–851 (1992).

Stryer, L., *Biochemistry,* Second Edition, (W.H. Freeman: San Francisco), pp. 200–202 (1981).

Philips, M.R. et al., "Up–regulation of the iC3b Receptor (CR3) is Neither Necessary Nor Sufficient to Promote Neutrophil Aggregation", *J. Clin. Invest.,* 82: 495–501 (1988).

Chemical Abstracts, entry for Registry No. 9072–19–9 (1995).

Patankar, M.S., "A Revised Structure for Fucoidan May Explain Some of Its Biological Activities", *J. Biol. Chem.,* 268(29): 21770–21776 (1993).

Nishino, T. et al., "Isolation and partial characterization of a novel amino sugar–containing fucan sulfate from commercial *Fucus vesiculosus* fucoidan", *Carbohydrate Research,* 255: 213–224 (1994).

Gooi, H.C. et al., "Stage–specific embryonic antigen involves α1→3 fucosylated type 2 blood group chains", *Nature,* 292: 156–158 (1981).

Han, K.T., et al., "Sialyl Lewis$^x$ Oligosaccharide Reduces Ischemia–Reperfusion Injury in the Rabbit Ear," *J. Immunol.,* 155:4011–4015 (1995).

Tuomanen, E., "A Spoonful of Sugar to Control Inflammation," *J. Clin. Invest.* 93:917–918 (1994).

Forsyth, K.D, et al., "CD15 Antibodies Increase Neutrophil Adhesion to Endothelium by an LFA–1–Dependent Mechanism," *Eur. J. Immunol,* 19:1331–1334 (1989).

Carlos, T.M. and Harlan, J.M., "Membrane Proteins Involved in Phagocyte Adherence to Endothelium," *Immunol. Reviews,* 1145–28 (1990).

Albrechtsen, M. and Kerr, M.A., "Characterization of Human Neutrophil Glycoproteins Expressing the CD15 Differentiation Antigen (3–fucosyl–N–acetyllactosamine)," *British J. of Heamat.,* 72:312–320 (1989).

Mulligan, M.S., et al., "Neutrophil–Dependent Acute Lung Injury," *J. Clin. Invest.,* 90:1600–1607 (1992).

Edington, S.M., "How Sweet It Is: Selectin–Mediating Drugs", *Biotechnology,* 10:383–389 (1992).

Gooi et al., Eur. J. Immunol. 13: 306–312 (1983).

METHOD OF INHIBITING PADGEM-MEDIATED OR ELAM-1-MEDIATED LEUKOCYTE ADHESION USING AN INHIBITOR COMPRISING A LE$^x$ CORE COMPONENT

This application is a continuation of application Ser. No. 08/230,862 filed Apr. 19, 1994 now abandoned, which is a File Wrapper Continuation of Ser. No. 07/667,030, filed Mar. 11, 1991, now abandoned.

GOVERNMENT SUPPORT

Studies described herein were supported in part by grant No. HL42443, awarded by the National Heart, Lung and Blood Institute. The government has certain rights in the invention.

BACKGROUND OF THE INVENTION

The LECCAMs or selectins, including Mel-14 antigen, LAM-1 (LECAM1), ELAM-1 (LECAM2), and PADGEM (LECAM3), are a newly recognized class of cellular adhesion molecules that are characterized structurally by the presence of a lectin-like domain, an epidermal growth factor-like domain, a variable number of cysteine-rich repeats related to those found in a family of complement regulatory proteins, a transmembrane domain, and a short cytoplasmic tail (Osborn, L., *Cell* 62: 306 (1990)). These cell adhesion molecules are thought to function in the adhesion of leukocytes to endothelial cells.

For example, the Mel-14 antigen and its human analog, LAM-1, which are present on the surface of lymphocytes, are thought to be involved in the targeting of lymphocytes to endothelial cells within high endothelial venules (Siegelman, M. H. et al., *Science*, 243: 1165–1172 (1989); Tedder, T. F. et al., *J. Exp. Med.*, 170: 123–133,(1989)). The endothelial leukocyte adhesion molecule-1, or ELAM-1, is synthesized and expressed on endothelial cells after stimulation with specific cytokines, and mediates the interaction of endothelial cells with neutrophils, monocytes and cell lines with monocyte-like features ((Bevilacqua, M. P. et al., *Proc. Natl. Acad. Sci. USA*, 84: 9238–9242 (1987); Bevilacqua, M. P. et al., *Science*, 243: 1160–1165 (1989); Hession, C. L. et al., *Proc. Natl. Acad. Sci. USA*, 87: 1673–1677, 1990).

The platelet activation dependent granule-external membrane protein, PADGEM, has been cloned and has a typical LECCAM structure, with a lectin domain, an epidermal growth factor domain, nine complement binding repeat domains, a transmembrane domain, and a cytoplasmic domain (Johnston, G. I. et al., *Cell*, 56: 1033–1044, (1989)). PADGEM, which is also referred to as GMP-140, CD62, or LECAM3, is found on the endothelial cell surface as well as on the surface of platelets. In endothelial cells, PADGEM is stored as a component of the Weibel-Palade bodies (Bonfanti, R. et al., *Blood* 73: 1109–1112, (1989)), and in platelets, it is stored as a component of the alpha granule membrane. Following granule exocytosis, PADGEM is expressed on the cell surface (Hsu-Lin, S. C. et al., *J. Biol. Chem.*, 259: 9121–9126, (1984); Berman, C. L. et al., *J. Clin. Invest.*, 78: 130–137 (1986); McEver, R. P. and Martin, M. N., *J. Biol. Chem.*, 259: 9799–9804, (1984); Stenberg, P. E. et al., *J. Cell Biol.*, 101: 880–886 (1985); Hattori, R. et al., *J. Biol. Chem.*, 264: 7768–7761 (1989)). PADGEM is also found in megakaryocytes, which are the precursors of platelets. (Beckstead et al., *Blood* 67: 285–293 (1986)).

Stimulated platelets bind to neutrophils and monocytes through specific recognition sites present on both cell types. This interaction is calcium dependent (Larsen, E. et al., *Cell* 59: 305–312 (1989); Hamburger, S. A. and McEver, R. P., *Blood*, 75: 550–554 (1990)). Studies demonstrating the inhibition of this interaction by anti-PADGEM antibodies or by purified PADGEM, indicate that PADGEM expressed on the platelet surface mediates this interaction (Larsen, E. et al., *Cell*, 59: 305–312 (1989)). Although the lectin-like domains of PADGEM and the other selectins show sequence similarity to calcium-dependent mammalian lectins (Drickamer, K., *J. Biol. Chem.*, 263: 9557–9560 (1988)), the natural ligands for the selectins have not been identified.

Certain carbohydrates are known to inhibit the interaction of the adhesion molecules with their natural ligands. For example, PPME, a mannose phosphate polysaccharide complex derived from yeast, and mannose 6-phosphate was reported to inhibit Mel-14-mediated lymphocyte-endothelial cell interaction (Stoolman, L. M. et al., *Blood* 70: 1842–1850 (1987)). Similarly, PADGEM-mediated binding of activated platelets to certain leukocytes is inhibited by heparin and fucoidin because of the interaction of these carbohydrates with PADGEM (Skinner, M. P. et al. *Biochem. Biophys. Res. Comm.*, 164: 1373–1379 (1989)).

SUMMARY OF THE INVENTION

The present invention relates to a method of inhibiting (reducing or preventing) the interaction or adhesion of platelets and/or endothelial cells with white blood cells (leukocytes) by contacting the platelets and/or endothelial cells with an inhibitor comprising a Lewis x (Le$^x$) core under conditions whereby adhesion is inhibited. By the method of the present invention, it is possible to inhibit the interaction of a PADGEM-bearing cell, such as a platelet or endothelial cell, with a cell bearing a PADGEM ligand (e.g., neutrophils and monocytes) by contacting the cell with an inhibitor comprising a Le$^x$ core component. As shown herein, antibodies directed against the CD15 cell surface antigen inhibit the interaction of PADGEM-bearing cells (e.g. platelets and COS cells bearing PADGEM) with leukocytes (e.g. neutrophils, monocytes). Furthermore, as is shown herein, Lacto-N-fucopentaose (LNF-III), a complex carbohydrate which comprises a Le$^x$ core component and is recognized by CD15 antibodies, inhibits the binding of stimulated platelets to neutrophils. Thus, the inhibitor can comprise a CD15 immunoreactive carbohydrate, such as Le$^x$ or all or portion of LNF-III. It will be appreciated that inhibitors useful in the present method comprise α(1-3)fucosylated lactosamine and polylactosamine derivatives.

DETAILED DESCRIPTION OF THE INVENTION

Figure 1:
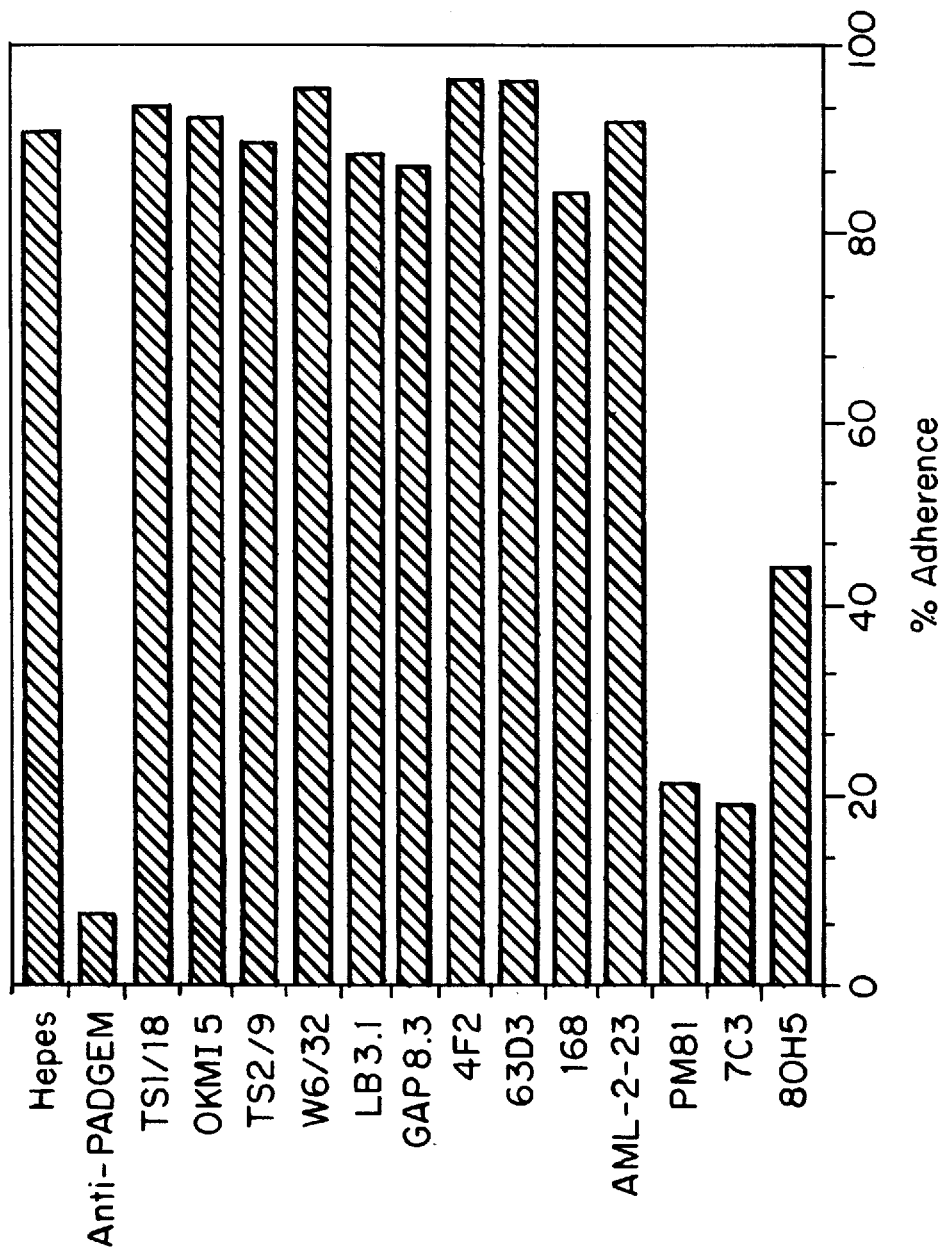
FIG. 1 illustrates the effects of a panel of anti-leukocyte antibodies on the interaction of neutrophils and activated platelets. The percent adherence corresponds to the percentage of cells with two or more adherent platelets under the assay conditions.

The present invention relates to a method of inhibiting (reducing or preventing) the interaction of a cell which bears a surface molecule that interacts with a ligand comprising a Le$^x$ core with its target ligand by contacting the cell with an inhibitor comprising a Lewis x (Le$^x$) core. The invention further relates to a method of inhibiting (reducing or preventing) the interaction or adhesion of endothelial cells and/or platelets with leukocytes (i.e., white blood cells), especially with nonlymphocytic leukocytes such as neutrophils and monocytes, by contacting the endothelial cells or platelets with an inhibitor comprising a Le$^x$ core. For example, it is possible to inhibit the interaction of a PADGEM-bearing cell, such as a platelet or endothelial cell, with a cell bearing a PADGEM ligand (e.g., neutrophils and monocytes) by contacting the PADGEM-bearing cell with an inhibitor comprising a Le$^x$ core component.

Identification of a PADGEM-ligand

To identify the natural PADGEM ligand on neutrophils and monocytes, a series of monoclonal antibodies prepared against a variety of leukocytes and derivative cell lines was surveyed to identify those that bind to structures on leukocytes, but do not bind to platelets, and those that also inhibit the interaction of activated platelets with leukocytes. Of the antibodies surveyed, only those directed against CD15 met these criteria. As shown in Example 3, antibodies directed against the CD15 cell surface antigen inhibit the interaction of PADGEM-bearing cells (e.g. platelets and COS cells bearing PADGEM) with leukocytes (e.g. neutrophils, monocytes). The observation that antibodies to CD15 blocked the interaction of activated platelets with neutrophils, monocytes, HL60 cells, and U937 cells suggested that CD15 on the white cell surface may be directly involved with or located in close proximity to the PADGEM ligand. In fact, several lines of evidence indicate that the PADGEM ligand actually shares structural features with CD15 positive structures.

CD15 is a carbohydrate antigen associated with glycolipids, glycoproteins, and proteoglycans (Kobata and Ginsburg, *J. Biol. Chem.,* 244: 5496–5502 (1969); Yang and Hakomori, *J. Biol. Chem.,* 246: 1192–1200 (1971); Huang et al., *Blood,* 61: 1020–1023 (1983); Skubitz and Snook, *J. Immunol.,* 139: 1631–1639 (1987); Christiansen and Skubitz, *Blood,* 71: 1624–1632 (1988)). This antigen is defined by a branched-chain oligosaccharide, LNF III (Huang et al., *Blood,* 61: 1020–1023 (1983). This pentasaccharide and its related isomers, LNF I and LNF II, are abundant in human milk (Kobata and Ginsburg, *J. Biol. Chem.,* 244: 5496–5502 (1969)). In addition to its distribution on neutrophils and monocytes, this carbohydrate is a marker for adenocarcinoma of the lung, colon and stomach, and for certain forms of lymphoma (Hall and Ardenne, *J. Clin. Pathol.,* 40: 1298–1304 (1987); Sanders et al., *J. Pathol.,* 154: 255–266 (1988)). The CD15 antigen is a component of glycolipids (Fukuda et al., *J. Biol. Chem.,* 260: 1067–1082 (1985)), glycoprotein O-linked oligosaccharides (Carlsson et al., *J. Biol. Chem.,* 261: 1287–12951986), and glycoprotein N-linked oligosaccharides (Fukuda et al., *J. Biol. Chem.,* 260: 12957–12967 (1985)) on human granulocytes. Specific glycoproteins present on the leukocyte surface have been shown to carry CD15 antigens and include LFA-1, Mac-1, gp150,95 (CD11/CD18), and CR1 (the C3b receptor) as well as proteins with molecular weights of 105,000 and 145,000 and a phosphotyrosine-containing protein of about 180,000 (Albrechtsen and Kerr, *Br. J. Haematol.,* 72: 312–320 (1989); Skubitz et al., *J. Immunol.,* 141: 4318–4323 (1988)). Although these proteins may be distributed among many vascular cell types, only on specific leukocytes, such as neutrophils and monocytes, do their structures include the complex carbohydrate LNF III.

Thus, the observation that three different anti-CD15 monoclonal antibodies inhibit the binding of activated platelets to monocytes and neutrophils, and that the distribution of CD15 on different vascular cells is parallel to the distribution of the PADGEM ligand, suggests that the PADGEM ligand and CD15 antigen are related. The demonstration in Example 3 that CD15 antibodies also inhibit the interaction of monocyte-like cells (U937) with COS cells transfected with PADGEM or with phospholipid vesicles containing purified PADGEM emphasizes the specificity of the anti-CD15 antibody inhibition for PADGEM mediated adhesion.

As shown in Example 4, purified forms of LNF III inhibit the interaction of activated platelets with neutrophils and monocytes. COS cells expressing PADGEM were shown to bind to HL60 and U937 cells, whereas COS cells not expressing PADGEM did not; this interaction was inhibited by LNF III or anti-CD15 antibodies (Example 4). Thus, inhibition by LNF III involves a process that is mediated by PADGEM on activated platelets.

Taken together, the data support a conclusion that LNF III or a portion thereof is a component of the PADGEM ligand. The LNF isomers are structurally closely related. They are composed of the same monosaccharides, but differ in the covalent linkages of these monosaccharides to form the pentassaccharide chain. LNF III binds more tightly to PADGEM, whereas LNF I demonstrates little or no interaction with PADGEM. LNF II, however, demonstrated slight inhibitory activity, particularly when the LNF to PADGEM ratio was high. Possibly minor contamination of the LNF II preparation with LNF III could account for this observation.

A comparison of the structure of LNF III, Galβ1-4 (Fucα1-3)GlcNAcβ1-3Galβ1-4Glc, to those of LNF I and LNF II (Fucα1-2Galβ1-3GlcNAcβ1-3Galβ1-4Glc, Galβ1-3 (Fucα1-4)GlcNAcβ1-3Galβ1-4Glc, respectively) indicates that the three carbohydrates share a common [GlcNAcβ1-3Galβ1-4Glc] trisaccharide moiety, but differ in the configuration of the fucosyl and galactosyl units at the non-reducing end. The preferential binding of LNF III to PADGEM suggests that LNF-III has features preferentially recognized by PADGEM. In particular, a Le$^x$ core, comprising Galβ1-4(Fucα1-3)GlcNAc, is unique to LNF III. This suggests that α1-3 fucosylated structures such as α1-3 fucosylated lactose or lactosamine are recognized by PADGEM.

The foregoing indicate that the PADGEM ligand comprises a CD15 immunoreactive carbohydrate, such as Le$^x$ or all or portion of LNF-III. An inhibitor comprising this structure or one which mimics the CD15 positive antigen on the surface of leukocytes can interfere with PADGEM-mediated interactions.

Inhibition of PADGEM-mediated Interactions

Figure 6:
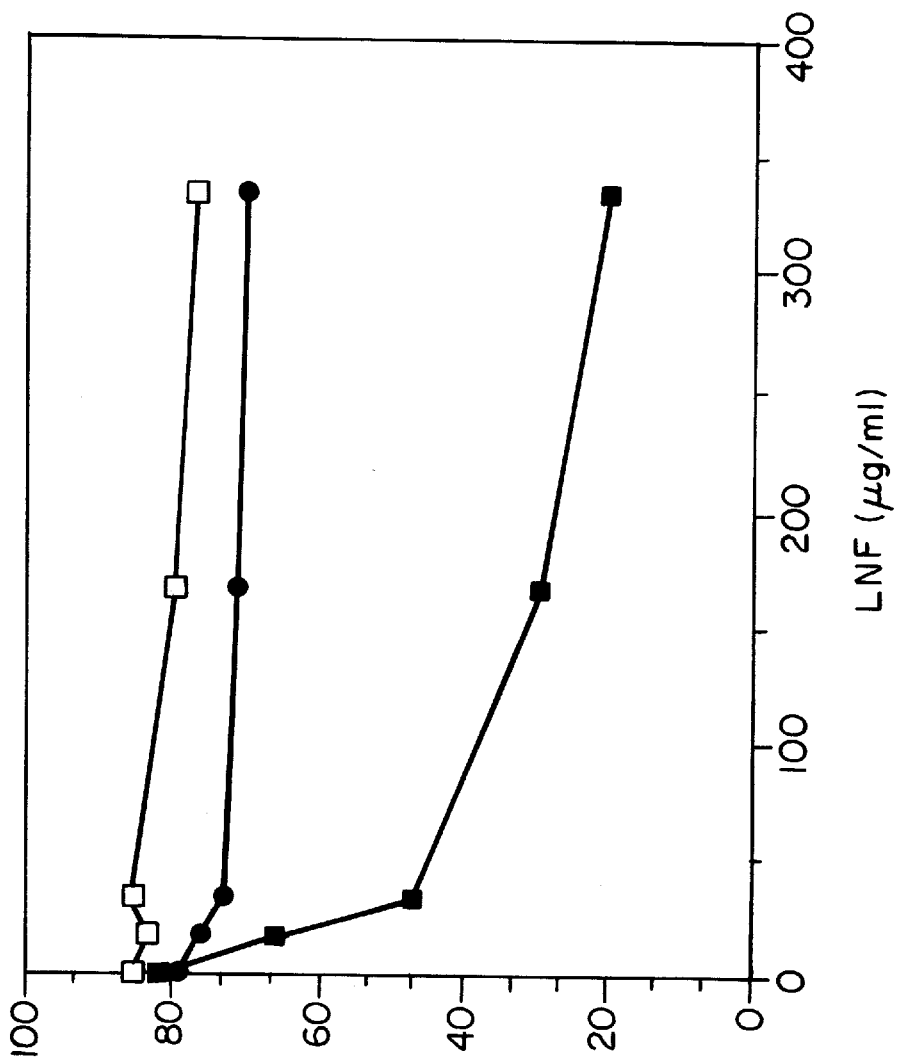
FIG. 6 illustrates the inhibitory effects of LNF isomers, LNF I (open squares), LNF II (closed circles), and LNF III (closed squares), on the interaction of activated platelets and neutrophils.
Figure 7:
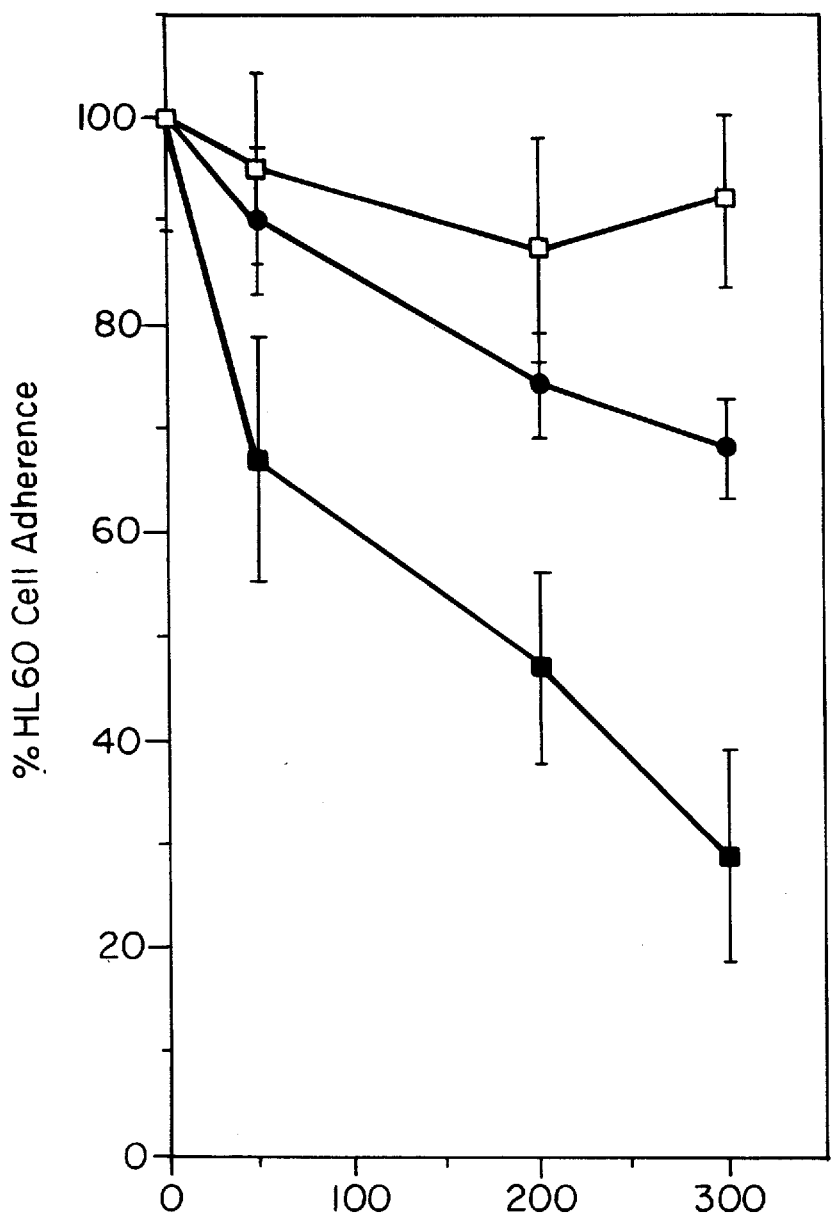
FIG. 7 illustrates the effects of LNF isomers LNF I (open squares), LNF II (closed circles), and LNF III (closed squares), on the interaction of HL60 cells with COS cells expressing PADGEM. Standard errors of triplicate experiments are given by the error bars.

In one embodiment, the interaction of a PADGEM-bearing cell (e.g., a platelet, an endothelial cell) with a cell bearing a PADGEM ligand, such as a neutrophil or a monocyte, is inhibited by contacting the PADGEM-bearing cell with an inhibitor comprising a Le$^x$ core component. For example, Lacto-N-fucopentaose (LNF III), a complex carbohydrate which comprises a Le$^x$ core component and is recognized by CD15 antibodies, inhibits the binding of stimulated platelets to neutrophils (FIG. 6). As shown herein, LNF III also inhibits the interaction of HL60 cells (monocyte-like cells) with COS cells that were transfected with PADGEM (FIG. 7). COS cells are fibroblast-like SV40-transformed African Green Monkey kidney cells. Therefore, LNF III inhibits the adhesion involving cells which naturally express PADGEM (e.g. nuetrophils and monocytes), as well as adhesion involving cells artificially induced to express PADGEM (e.g. PADGEM-transfected cells). Thus, the inhibitor can comprise a CD15 immunoreactive carbohydrate, such as LNF III.

It will be appreciated, that a molecule which interacts with a ligand comprising a Le$^x$ core need not be associated with a cell (e.g., present at the cell surface as a transmembrane protein) for inhibition of the interaction with its target ligand to occur. The interaction may be inhibited by contacting the molecule with an inhibitor comprising a Lewis x (Le$^x$) core. For example, a cDNA encoding a form of PADGEM which lacks the transmembrane region has been isolated from a human umbilical vein endothelial cell cDNA library (Johnston, et al., *Cell* 56: 1033–1044) and soluble forms of PADGEM can be constructed using recombinant techniques. The interaction of such truncated versions of PADGEM with a PADGEM-ligand can also be inhibited, reduced or prevented using an inhibitor comprising a Le$^x$ core. This method can be useful in counteracting the effect of soluble forms of PADGEM.

Inhibitors of Leukocyte Adhesion

Inhibitors useful in the present method can be identified by their ability to inhibit (reduce or prevent) the interaction of a surface molecule that interacts with a ligand comprising a Le$^x$ core (e.g., PADGEM) with its target ligand. The surface molecule can be in several forms, including, but not limited to, a soluble form, incorporated into a vesicle, such as a liposome or phospholipid vesicle, or associated with a cell (e.g., as a transmembrane protein). Ligands can also be in several forms, including, but not limited to, a soluble form or associated with a cell (e.g., attached to a cell surface structure such as a glycoprotein or glycolipid).

Similarly, inhibitors of the interaction of a surface molecule that interacts with a ligand comprising a Le$^x$ core with its target ligand can also be in several forms. Inhibitors useful in the present method comprise a Le$^x$ core component. The inhibitors can be a branched trisaccharide or larger carbohydrate comprising a Le$^x$ core component. Additional sugars and/or functional groups can be added to the Le$^x$ core consistent with inhibitory activity. As used herein, a Le$^x$ core component refers to a structure comprising a Le$^x$ antigen (e.g., Galβ1-4(Fucα1-3)NAcGlc, an α(1-3)fucosylated lactosamine) or other α(1-3)fucosylated lactosamines exhibiting similar biological function. In addition, a Le$^x$ core refers to a structure comprising a structural analog of a Le$^x$ antigen, which, alone or as a component of an inhibitor, can inhibit (reduce or prevent) the interaction of a surface molecule that interacts with a ligand comprising a Le$^x$ core (e.g., PADGEM) with its target ligand. Thus, useful inhibitors can comprise a CD15 immunoreactive carbohydrate comprising a Le$^x$ core, although the inhibitor itself need not be CD15 immunoreactive. Examples of CD15 immunoreactive carbohydrates comprising a Le$^x$ core are LNF III, or a portion of LNF III comprising a Le$^x$ core, and a Le$^x$ antigen. Inhibitors comprising a Le$^x$ core also include, but are not limited to, Le$^x$ antigens (e.g., Galβ1-4(Fucα1-3)NAcGlc), LNF-III, or a portion thereof, or other α(1-3) fucosylated lactosamines.

CD15 antigen is a component of glycolipids, glycoprotein O-linked oligosaccharides, and glycoprotein N-linked oligosaccharides on human granulocytes. It is possible that additional carbohydrate, protein or lipid structures of the actual ligand or ligands contribute to the interaction with surface molecule such as PADGEM, and enhance the specificity of the interaction. Thus, useful inhibitors can comprise, for example, a protein or peptide, with a carbohydrate moiety comprising a Le$^x$ core (e.g., a glycoprotein with N-linked and/or O-linked oligosaccharide(s)). For example, Galβ1-4(Fucα1-3)NAcGlc- can be linked to a protein via the NAcGlc (N-acetylglucosamine) moiety or incorporated into a larger saccharide chain on a protein. Alternatively, inhibitors can comprise a lipid portion (e.g., a phospholipid, ceramide, or sphingolipid). Inhibitors comprising more than one Le$^x$ core may have enhanced activity due to multivalency. Inhibitors useful in the method (e.g., glycoproteins, glycolipids, carbohydrates) can also be incorporated into a lipid vesicle (e.g., phospholipid vesicle or liposome).

Inhibitors can be purified from natural sources. For example, sialylated fucosyl lactosaminoglycans can be isolated from granulocytes (Fukuda, et al., *J. Biol. Chem.* 259: 10,925–10,935 (1984)). Alternatively, they can be synthesized chemically or enzymatically using techniques known in the art (Toone, E. et al., *Tetrahedron Rep.*, 45: 5365–5422 (1989); Wong, C. -H., *Science*, 244: 1145–1152 (1989)).

The activity of an inhibitor may be determined using an appropriate assay. For example, the adhesion assays described in Example 2 can be used to assay the inhibitory activity of candidates upon PADGEM-mediated adhesion. Alternatively, a candidate inhibitor may be identified by its ability to interfere with the interaction between another identified inhibitor (e.g., LNF III) and PADGEM (e.g., purified PADGEM, PADGEM on a cell, PADGEM in a liposome) in a competitive binding assay.

Methods of Therapy

The cellular adhesion molecules PADGEM and ELAM-1 are thought to be involved in the recruitment of neutrophils and monocytes to sites of inflammation. Moreover, PADGEM, which is also present in platelets is thought to have an important role in the clotting process. By inhibiting (reducing or preventing) the interaction or adhesion of endothelial cells and/or platelets with white blood cells (i.e., leukocytes, such as monocytes and neutrophils) by the method of the present invention, it is possible to interfere with the processes that these cell interactions mediate or participate in.

For example, in one embodiment, the inhibition of the interaction of activated platelets with neutrophils and monocytes is inhibited by contacting the platelets with an inhibitor comprising a $Le^x$ core. Activated platelets can bind to injured endothelial and subendothelial surfaces through mechanisms involving glycoprotein Ib and von Willebrand factor. The expression of PADGEM on these platelets at the site of vascular injury could lead to the binding of monocytes and neutrophils. The latter cells are capable of initiating the tissue factor-mediated extrinsic pathway of blood coagulation. However, the inhibitors of this invention can interfere with platelet-neutrophil or platelet-monocyte interactions to block adhesion and thereby interrupt the coagulation process. Thus, it is possible to inhibit pathological thrombosis using the present method.

In another embodiment, activated platelets or endothelial cells at the site of tissue injury or inflammation could recruit leukocytes from the blood stream, resulting in the release of inflammatory mediators and causing further tissue damage. For example, where PADGEM-mediated interactions have a role in inflammation, an inhibitor comprising a $Le^x$ core can inhibit the adhesion of monocytes and neutrophils to platelets or endothelial cells, to prevent or minimize inflammation. Thus, autoimmune and inflammatory diseases or conditions can be treated by the present method.

Tissue injury, such as neutrophil-mediated ischemia-reperfusion damage due to blood vessel occlusion and reperfusion could be inhibited by interfering with adhesion of neutrophils. Contacting platelets bearing PADGEM with an inhibitor comprising a $Le^x$ core can inhibit neutrophil adhesion, minimizing damage in the region of the thrombus. Treatment with clot-dissolving drug, such as tissue plasminogen activator or streptokinase, can be accompanied by treatment with an inhibitor comprising a $Le^x$ core to inhibit reperfusion injury. At the same time, the inhibitor can also act together with clot-dissolving drugs to inhibit clotting.

In a model of atherosclerosis, injured endothelial cells in a vessel wall express PADGEM on their surface. Monocytes bearing a PADGEM ligand are recruited to the site by virtue of PADGEM—PADGEM ligand interaction, and adhere to the endothelial cells. The monocytes become pathological foam cells by ingestion of lipids, platelet fragments, and other molecules. However, the atherosclerotic process can be inhibited by contacting the PADGEM-bearing endothelial cells with an inhibitor comprising a $Le^x$ core, which inhibits PADGEM-mediated adhesion.

CD15 antigen, comprising a $Le^x$ core, is a marker for adenocarcinoma of the lung, colon and stomach, and for certain forms of lymphoma (Hall and Ardenne, J. Clin. Pathol., 40: 1298–1304 (1987); Sanders et al., J. Pathol., 154: 255–266 (1988)). It is possible that cell adhesion processes play a role in metastasis. For example, ELAM-1 supports the adhesion of a human colon carcinoma cell line to endothelial cells (Rice and Bevilacqua, Science, 246: 1303–1306 (1989)). Adhesion to vessel walls and estravasation by certain tumor types may be facillitated by their expression of a ligand for PADGEM or another endothelial cell surface molecule capable of interacting with a $Le^x$ core. It is possible to disrupt the metastatic process by disrupting the interaction of such surface molecules with CD15 or $Le^x$ antigens on tumor cells by the method of the present invention.

For use in treating a condition in an individual in which a surface molecule capable of interacting with a $Le^x$ core plays a role in pathological process (e.g., atherosclerosis, thrombolysis, inflammation, or metastasis), inhibitors of the present invention are administered by an appropriate route (e.g., intravenously, parenterally or topically). Treatment is under appropriate conditions and in amounts sufficient to reduce or prevent adhesion and thereby, reduce or prevent the disease process. For example, an inhibitor can be combined with a suitable carrier, incorporated into a liposome, or polymer release system for administration.

The invention is further and more specifically described in the following examples.

EXAMPLES

The reagents and cell preparation procedures below were used in the following examples.

Reagents

Antibody 80H5 was purchased from AMAC, Inc. Other antibodies were the generous gifts of Drs. Dennis Hickstein and John Harlan (7C3), Dr. Paul Guyre (PM81, 168, AML-2-23), and Dr. Douglas Faller (TS1/18, OKM15, TS2/9, W6/32, LB3.1, GAP8.3, 4F2, and 63D3). Polyclonal anti-PADGEM antibodies were raised in rabbits and isolated by affinity chromatography on PADGEM-Sepharose, as previously described (Berman et al., J. Clin. Invest., 78: 130–137 (1986)). The monoclonal anti-PADGEM antibody AC1.2 has been previously described (Larsen et al., Cell 59: 305–312 (1989)). LNF I, LNF II, and LNF III, purchased from Calbiochem, were greater than 95% pure by HPLC, as assayed by the supplier.

Isolation of Cells

Platelets were isolated by gel filtration from fresh anti-coagulated blood obtained from normal human donors (Hsu-Lin et al., J. Biol. Chem., 259: 9121–9126 (1984)). Activated platelets were prepared by incubating cells without stirring for 20 minutes at 22° C. with thrombin at a final concentration of 0.25 U/ml. Fresh platelets were used in cell adhesion assays within 30 minutes of preparation.

Neutrophils were prepared by the method of English and Anderson (J. Immunol. Method, 5: 249–252 (1974)). The neutrophil preparations were greater than 95% pure by light microscopy. Monocytes were prepared by washing the mono-nuclear leukocyte fraction twice with human serum-5 mM EDTA and incubating the cells in RPMI 1640—10% fetal calf serum in sterile plasmid dishes for 2 hours at 37° C. The dishes were washed three times with PBS at 37° C. to remove nonadherent cells. PBS at 0° C. was added, and the cells were incubated at 4° C. for 1 hour. Adherent cells were gently detached with a rubber policeman, washed in PBS, and resuspended in RPMI 1640—1% fetal calf serum. Lymphocytes were obtained by washing the nonadherent cells with PBS and resuspending these cells in RPMI 1640—1% fetal calf serum. The purity of these preparations was established to be greater than 90% by light microscopy using Wright esterase and nonspecific esterase stains.

Cell lines HL60 and U937 were maintained in culture in RPMI 1640 medium supplemented with penicillin G sodium (100 U/ml), streptomycin sulfate (100 µg/ml), HEPS (10 mM), sodium pyruvate (1 mM), L-glutamine (2 mM), β-mercaptoethanol (0.0004%), and 10% fetal calf serum.

EXAMPLE 1

Cloning of PADGEM and Expression in COS Cells

The PADGEM cDNA was cloned from a human umbilical vein cDNA library in λgt11 using oligonucleotides based upon the published DNA sequence (Johnston et al., Cell 56: 1033–1044 (1989)). Approximately $3 \times 10^6$ plaques from an oligo(dT)-primed human umbilical vein endothelial cell cDNA library were transferred to nitrocellulose filters for screening. Duplicate filters were hybridized with either a $^{32}$P-labeled 24 nucleotide probe derived from the 5' end of the translated sequence or one from the 3' end of the translated sequence (Johnston et al., *Cell* 56: 1033–1044 (1989)). Of six clones that were positive with both probes, only one appeared to be a full-length cDNA. Sequencing demonstrated that the latter clone lacked 56 bases from the 5' end of the translated sequence. One of the base differences from the original published sequence, a T to C change at position 99, resulted in an additional EcoRI site that may be responsible for the 56 base deletion. The partial PADGEM CDNA was rendered full length by ligating to it a synthetic DNA fragment containing the 56 bp of missing sequence.

The sequence of the full-length PADGEM cDNA was established in its entirety. The nucleotide sequence obtained was identical to that of Johnston et al. (*Cell* 56: 1033–1044 (1989)), with the exception of five nucleotides within the coding sequence: T at 1088, C at 1832, C at 1850, C at 99, and C at 859. The latter two sequence differences result is amino acid sequence differences, such that a proline is encoded at residue −21 instead of serine, and a threonine is encoded at residue 233 instead of isoleucine. The other three base changes do not alter the predicted amino acid sequence. The full-length PADGEM cDNA was inserted into a modified form of the expression vector CDM8 (Tedder and Isaacs, *J. Immunol.*, 143: 712–717 (1989)).

COS cells ($1 \times 10^5$) were transfected with 40 μg of the resulting PADGEM expression vector by calcium phosphate precipitation. Coverslips (12×12 mm) were added to each culture. After 48 hours of growth in DMEM—10% fetal calf serum, the COS cells were confluent.

The presence of PADGEM expression in the transfected COS/PADGEM cells was demonstrated by immunofluorescent staining using the monoclonal antibody AC1.2. Cells were incubated with the anti-PADGEM monoclonal antibody AC1.2 (Bonfanti et al., *Blood* 73: 1109–1112 (1989)) and stained with rhodamine conjugated to goat anti-mouse antibody. The immunoflourescence data indicated that, in these experiments, 10%–20% of the COS cells expressed PADGEM. Furthermore, HL60 cells, from a human cell line that exhibits monocyte-like characteristics, and which bind to platelets in a PADGEM-dependent manner (Larsen, E. et al., *Cell* 59: 305–312 (1989)) were found to bind to COS cells expressing PADGEM (COS/PADGEM transfectants). In contrast, the HL60 cells did not bind to COS cells that were subjected to mock transfection. These results indicated that the COS-PADGEM transfectants retain adhesive properties of PADGEM.

EXAMPLE 2

Cell Adhesion Assays

Phase-contrast Assay

Twenty microliters of platelet suspension ($2 \times 10^8$/ml) was mixed with 20 μl of cell suspension ($2 \times 10^6$/ml) and incubated for 20 minutes at 22° C. in a microfuge tube. An aliquot of the cell suspension was then in a Neubauer chamber and evaluated by light microscropy using an Olympus model BH-2 microscope. Three samples from each assay were evaluated by counting 200 cells and scoring the percentage of cells with two or more adherent platelets (Jungi et al., *Blood* 67: 629–636 (1986)). Antibody inhibition studies were performed by preincubating cells (20 μl; $3 \times 10^6$/ml) with 20 μl of antibody solution for 20 minutes at 22° C. Subsequently, 20 μl of platelet suspension was added, and the mixture was incubated for 20 minutes at 22° C. Samples were analyzed as above.

COS Cell-PADGEM Adhesion Assays

HL60 cells ($1 \times 10^7$), maintained in culture, were washed and resuspended in 0.5 ml of serum-free RPMI 1640. The cells were labeled with 270 μCi of $^{111}$In oxine (Callow et al., *Arch. Surg.*, 117: 1447–1455 (1982)) and 10 μg of bis-carboxyethyl-carboxyfluorescein (Kolber et al., *J. Immunol. Meth.*, 108: 255–264 (1988)) by incubation at 37° C. for 30 minutes. After washing with RPMI 1640—1% bovine serum albumin, the cells ($1 \times 10^6$) were incubated with the coverslips containing confluent COS cell transfectants, in the presence or absence of LNF isomers, for 20 minutes at 37° C. The coverslips were washed with RPMI 1640, and duplicate coverslips were assayed for $^{111}$In activity. Alternatively, samples were evaluated for HL60 cell adherence by fluorescence and phase-contrast microscopy using a Zeiss Axioscope microscope in a blind assay. Inhibition of the binding of COS/PADGEM cells to U937 cells by the antibody 80H5 was performed in experiments identical to the procedure described above.

CHO-ELAM and CHO-PADGEM Adhesion Assay

Chinese hamster ovary cells (CHO-DUKX) were transfected with cDNA encoding ELAM or PADGEM to make CHO-ELAM and CHO-PADGEM cells. Each of the following cell types, Chinese hamster ovary cells-DUKX (CHO-DUKX), Chinese hamster ovary cells transfected with cDNA for ELAM (CHO-ELAM) and Chinese hamster ovary cells transfected with cDNA for PADGEM (CHO-PADGEM), were separately plated at a density of $6 \times 10^4$ cells per milliliter of medium into Costar 48 well culture plates. On the following day, HL60 cells in culture were sedimented by centrifugation and resuspended in medium (RPMI, 10% fetal calf serum) to a density of $5 \times 10^5$ cells/ml. Tritiated thymidine (5 μCi per milliliter) was added to the HL60 cell suspension and the cells were grown overnight. The following day the HL60 cells were washed thrice in serum free RPMI and resuspended in a volume of 5 mls of RPMI. After assuring that the free tritium in the cell suspension is no more than 10% of the cell associated tritium, the cell count of the cell suspension was established and the cell density was adjusted to $1 \times 10^6$ cells per milliliter.

To perform the assay medium was aspirated from the CHO cells, CHO-ELAM cells and CHO-PADGEM cells. The wells containing these cells were rinsed with 1 ml of serum free RPMI. HL60 cells were preincubated for 10 minutes with the test sugar at the concentrations indicated. Aliquots of these HL60 cells (100,000 to 300,000 cells) were then added to individual wells containing CHO cells of the various types and the two cell populations incubated together for 30 minutes at room temperature. Unbound HL60 cells were removed by aspiration and the wells were washed thrice with serum free RPMI. The adherent CHO cells and any bound HL60 cells were detached from the surface of the wells with 250 μl of phosphate buffered saline containing 1 mM EDTA. An aliquot of the detached cells (200 μl) was analyzed for tritium content in a β-scintillation counter. The level of nonspecific binding of tritiated HL60 cells was taken as the level of binding seen in the wells containing the CHO-DUKX cells (parent cell line of CHO-PADGEM and CHO-ELAM transfectants). This value was subtracted from the level of tritiated HL60 cells bound in wells containing CHO-ELAM or CHO-PADGEM cells. The decrease in binding induced by the presence of the sugar was determined by comparing the level of binding of HL60 cells in the presence of the sugar to that observed in its absence.

Binding of U937 Cells to Phospholipid Vesicles Containing PADGEM

PADGEM was incorporated into phospholipid vesicles as previously described (Larsen et al., *Cell* 59: 305–312

(1989)) with some modifications. Briefly, 5 mg of egg phosphatidylcholine (Avanti Polar Lipids) and 0.025 mg of Di $IC_{16}(3)$ (1,1'-dihexadecyl-3,3,3',3'-tetramethyl-lindocarbocyanine perchlorate) (Molecular Probes) in chloroform were mixed, and the chloroform was removed by evaporation at 37° C. under nitrogen. The dried lipids were resuspended in methylene chloride, and the solvent was removed by evaporation. Purified PADGEM (1 ml; 65 µg/ml; Larsen et al., Cell 59: 305–312 (1989)) in Tris-buffered saline containing 50 mM octyl-β-D-glucopyranoside (Calbiochem) or Tris-buffered saline along containing 50 mM octyl-β-D-glucopyranoside (1 ml) was added to the dried phospholipids, and the lipids were resuspended. The preparations were dialyzed under nitrogen against Tris-buffered saline-0.02% $NaN_3$ for 24 hours. Vesicles were separated from free protein by gel filtration on a Sepharose 4B column. Phospholipid vesicles (50 µl) with or without PADGEM were incubated with $2 \times 10^5$ U937 cells in RPMI 1640, 1% fetal calf serum, 2% bovine serum albumin for 30 minutes at 23° C. For experiments with 80H5 antibody, U937 cells were incubated with the antibody (5 µg/ml) for 1 hour; phospholipid vesicles were added, and the incubation was continued for an additional 30 minutes. Prior to analysis on a FACScan (Becton Dickinson), each sample was diluted 10 fold with RPMI 1640, 1% fetal calf serum, 2% bovine serum albumin. U937 cells were identified by their forward and side light scatter profiles, and binding of PADGEM in phospholipid vesicles was quantitated by measuring red fluorescence. Data were collected for 3000 cells.

EXAMPLE 3

Anti-CD15 Antibodies Inhibit the Platelet-Leukocyte Interaction

Effects of Anti-Leukocyte Antibodies on the Interaction of Activated Platelets with Neutrophils, Monocytes, HL60 Cells, and U937 Cells Thrombin-activated platelets bind to human neutrophils, monocytes, HL60 cells and U937 cells in an interaction that is mediated by PADGEM on the surface of the platelet (Larsen et al., Cell 59: 305–312 (1989). This interaction is inhibited by anti-PADGEM antibodies and purified PADGEM. Unstimulated platelets, which do not express PADGEM on the platelet surface, do not interact with these leukocytes.

Figure 2:
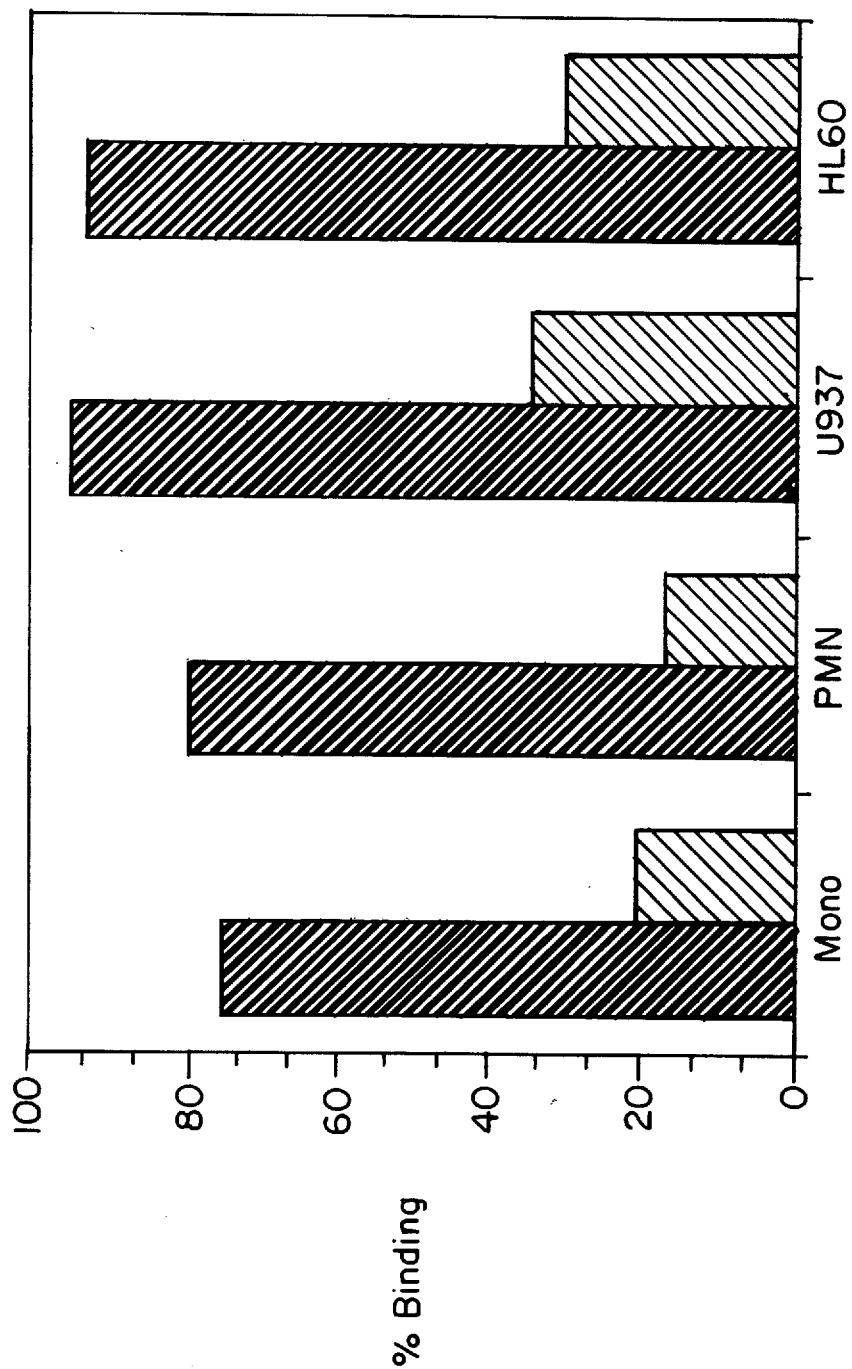
FIG. 2 illustrates the inhibitory effects of 80H5 monoclonal antibody on the interaction of thrombin-stimulated platelets with monocytes (Mono), neutrophils (PMN), U937 cells (U937) and HL60 cells (HL60). The height of the bar indicates the percent binding or percentage of cells with two or more adherent platelets in the absence of antibody (black bars) or in the presence of antibody (hatched bar).

To identify the PADGEM recognition site on leukocytes that mediates the binding of activated platelets, monoclonal antibodies directed at various antigens on the surface of monocytes and neutrophils were tested for their ability to inhibit the interaction of these cells with activated platelets, using the phase-contrast cell adhesion assay described in Example 2 (FIG. 1 and FIG. 2). The antibodies were raised against various leukocytes and myeloid cell lines and are directed at leukocyte antigens. The antibodies which were tested and their corresponding antigens are as follows: TS1/18, LFA-1 (β); OKM15, CR3; TS2/9, LFA-3; W6/32, HLA class I; LB3.1, HLA class II; GAP8.3, T200; 4F2, 4F2; 63D3, 63D3; 168, 168; AML-2-23, 2-23; PM81, CD15; 7C3, CD15; 80H5, CD15. These immunochemical reagents included antibodies of the IgG and IgM isotype. The effect of buffer alone (HEPES) on the adherence of activated platelets and neutrophils served as a negative control, while the effect of anti-PADGEM antibodies on cell adherence served as a positive control for inhibition. The percentage of cells displaying two or more adherent platelets was determined as described in Example 2.

With the exception of antibodies which recognize CD15 (PM81, 7C3, and 80H5), none of the other antibodies that were tested demonstrated inhibitory properties. The anti-CD15 monoclonal antibodies, obtained from three separate and independent hybridoma cell lines and of the IgM isotype, each displayed significant inhibition of the interaction between neutrophils and activated platelets (FIG. 1). These results suggest that the anti-CD15 antibodies are targeted against a structure on the leukocyte surface which participates in the PADGEM-mediated binding of leukocytes to activated platelets.

The effect of 80H5 antibodies against CD15 on the interaction of activated platelets with neutrophils, HL60 cells, U937 cells, or monocytes is illustrated in FIG. 2. In the absence of anti-CD15 antibodies (black bars), activated platelets adhered to neutrophils (PMN). However, this binding was inhibited with anti-CD15 antibodies. Similarly, the 80H5 antibody blocked the interaction of activated platelets with monocytes (Mono), U937 cells, and HL60 cells. These leukocytes are known to be CD15 positive, and anti-CD15 antibody was observed to inhibit cell adhesion with thrombin stimulated platelets in each case. In contrast, we confirmed that platelets, which carry PADGEM, but which apparently lack the PADGEM ligand, are CD15 negative. Thus, the distribution of CD15 positivity parallels the expression of PADGEM recognition sites on specific leukocytes (Larsen et al., Cell 59: 305–312 (1989)). Just as anti-PADGEM antibodies directed against PADGEM on platelets can inhibit platelet-leukocyte interaction, anti-CD15 antibodies directed against CD15 on leukocytes inhibit platelet-leukocyte interaction.

Inhibition of PADGEM-Leukocyte Binding with CD15 Antibodies

Figure 3:
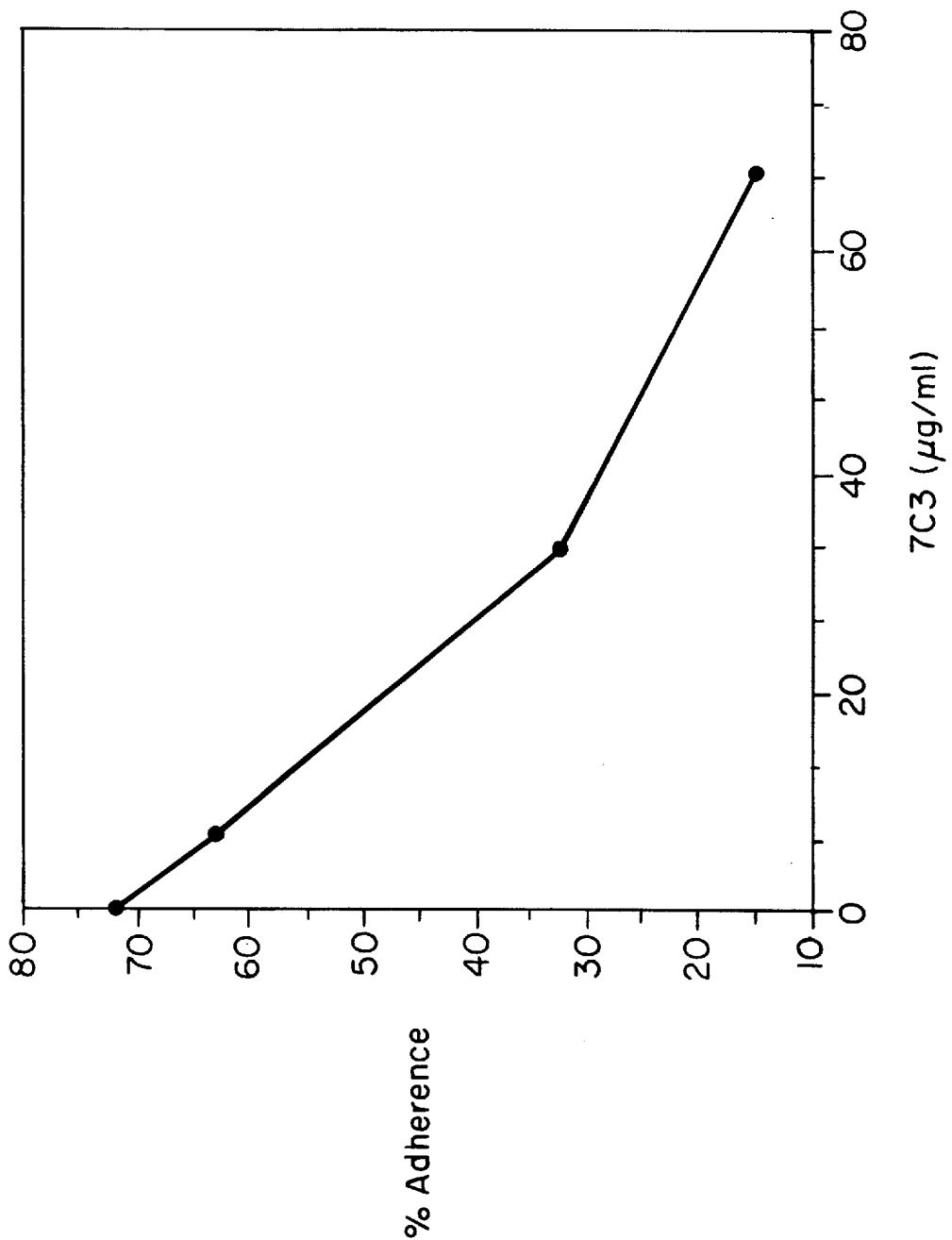
FIG. 3 illustrates the effect of the concentration of anti-CD15 antibody 7C3 on the inhibition of the binding of activated platelets to neutrophils. The percent adherence corresponds to the percentage of cells with two or more adherent platelets under the assay conditions.

The inhibition of activated platelet adherence to neutrophils by anti-CD15 antibody was dependent upon the concentration of antibody. Using the anti-CD15 antibody 7C3 (Nauseef et al., Blood 62: 636–644 (1983)) in the phase-contrast adhesion assay (Example 2), half-maximal inhibition was observed at about 30 µg/ml (FIG. 3). Although complete inhibition was not observed, inhibition to the extent of 60%–80% was observed in multiple, independent experiments. Similar results were obtained with other anti-CD15 antibodies, including PM81 and 80H5, or with different cells, including monocytes, HL60 cells, and U937 cells (data not shown). It has been previously demonstrated that the binding of leukocytes (including neutrophils, monocytes, HL60 cells, and U397 cells) to activated platelets is mediated by PADGEM (Larsen, E. et al., Cell 59: 305–312 (1989)). The results shown here suggest that antibodies to CD15, which disrupt cell—cell interactions which are mediated by PADGEM, are directed toward the PADGEM ligand.

Figure 4:
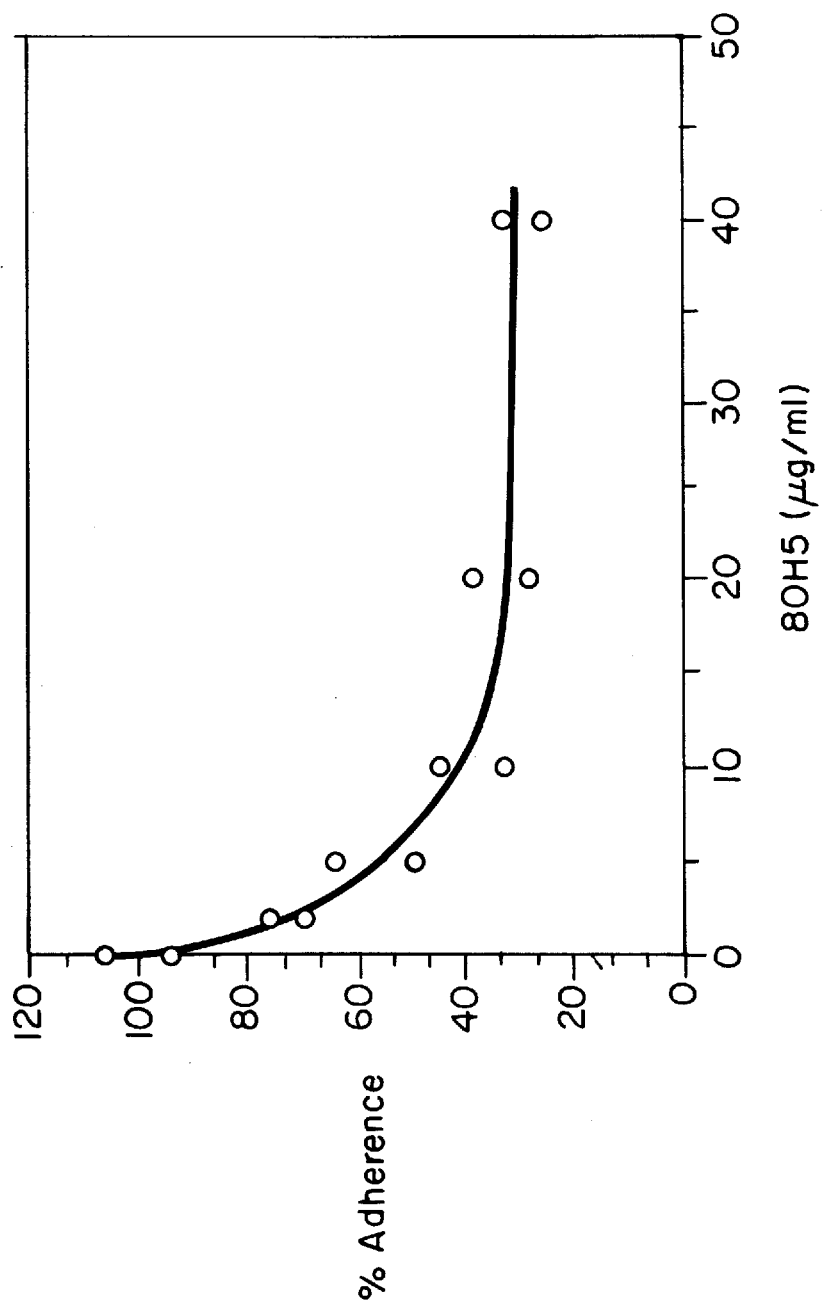
FIG. 4 illustrates the inhibition of adherence of $^{111}$In-labelled U937 cells to COS/PADGEM cells by monoclonal antibody 80H5 as assayed by counting $^{111}$In activity.

To confirm that the inhibitory activity of the anti-CD15 antibodies involves the PADGEM ligand specifically, the effect of anti-CD15 antibodies on the binding of COS/PADGEM cells to $^{111}$In-labeled U937 cells was studied. COS/PADGEM cells were constructed as described in Example 1. The COS cell-PADGEM adhesion assay is described in Example 2. As shown in FIG. 4, anti-CD15 antibody 80H5 inhibited COS/PADGEM binding to U937 cells, indicating that the anti-CD15 antibodies specifically interfere with PADGEM-mediated interactions. These results further emphasize that the anti-CD15 antibodies are directed against the PADGEM ligand, and not a ligand of other proteins that have been implicated in platelet-leukocyte interaction (Silverstein and Nachman, J. Clin. Invest., 79: 867–874 (1987)).

Figure 5:
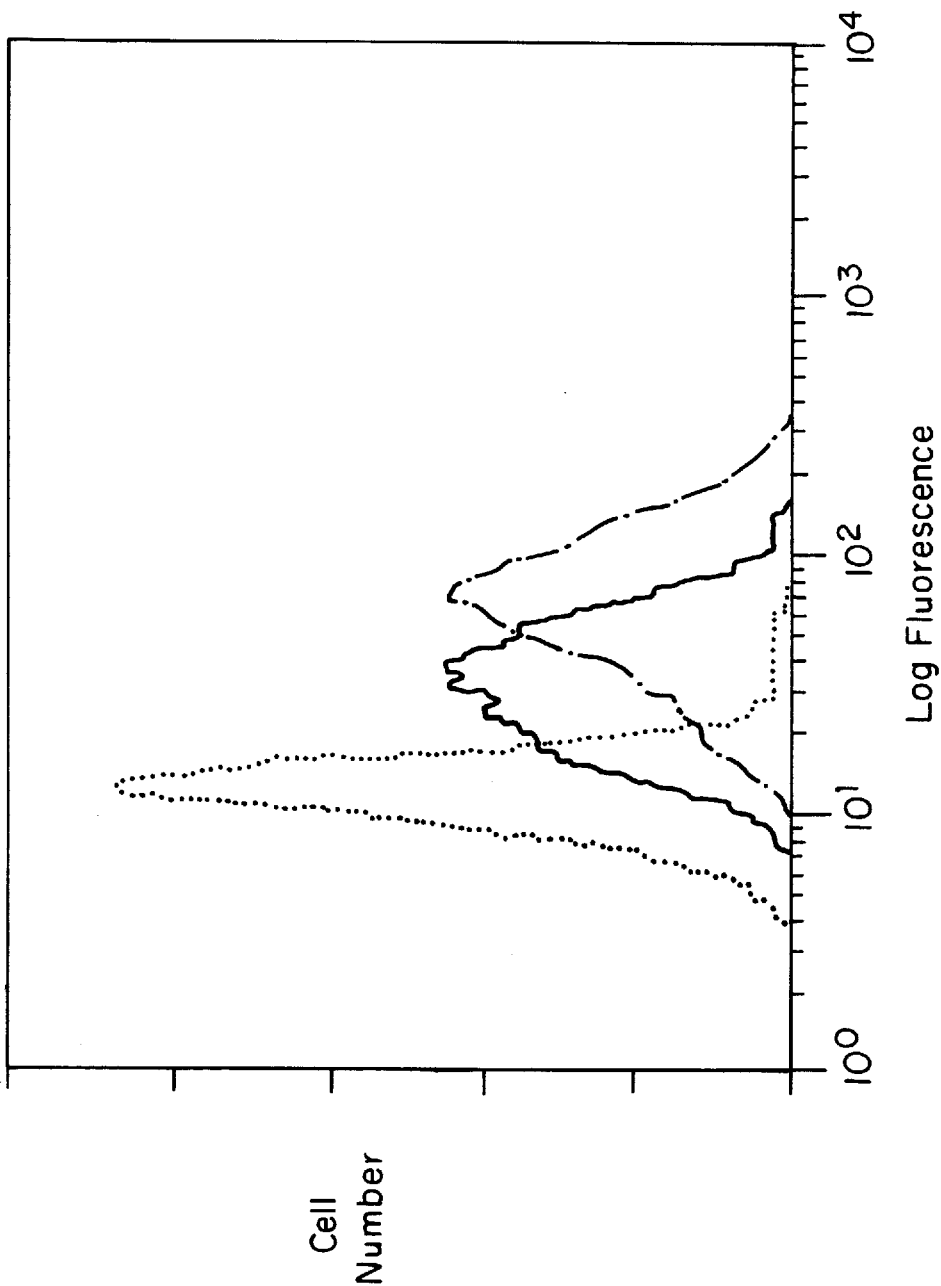
FIG. 5 illustrates the results of a FACS analysis of the interaction of U937 cells with phospholipid vesicles containing purified PADGEM. A histogram of log red fluorescence is given on the X axis and cell number is given on the Y axis. U937 binding to phospholipid vesicles without PADGEM (dotted line), to phospholipid vesicle containing PADGEM (dashed and dotted line), and to phospholipid vesicles containing PADGEM in the presence of anti-CD15 antibody (solid line) is shown.

To demonstrate further that the anti-CD15 antibody inhibition of leukocyte-platelet interaction was mediated via PADGEM, the effect of antibodies against CD15 on the binding of PADGEM-containing phospholipid vesicles to U937 cells was determined. Purified PADGEM was incorporated into fluorescently labelled phospholipid vesicles and adhesion of vesicles to U937 cells was monitored on a fluorescence-activated flow cytometer as described in Example 2. As shown in FIG. 5, anti-CD15 antibodies inhibited the interaction of U937 cells with phospholipid vesicles containing PADGEM. Phospholipid vesicles lacking PADGEM did not interact with U937 cells, confirming previous results (Larsen et al., Cell 59:305–312 (1989)). These results indicate that PADGEM is the complementary structure that is recognized by the target of the anti-CD15 antibody.

EXAMPLE 4

Inhibition of PADGEM-Mediated Platelet-Leukocyte Interaction by Lacto-N-Fucopentaose III CD15 antigen has been identified as a complex carbohydrate; CD15 antibodies react with lacto-N-fucopentaose III (LNF III). This carbohydrate has the structure GAl$\beta$1-4(Fuc$\alpha$1-3)GlcNAc$\beta$1-3Gal$\beta$1-4Glc. If the anti-CD15 antibody inhibits the interaction of stimulated platelets and leukocytes by binding the PAGDGEM recognition site of leukocytes, thus precluding the binding of PADGEM on platelets, purified CD15 antigen (e.g., LNF III) should also inhibit platelet-leukocyte interaction, since it would saturate the binding sites on PADGEM.

As shown in FIG. 6, LNF III was an effective inhibitor of the adherence of activated platelets to neutrophils, as determined using the direct cell adhesion assay (closed squares). Half-maximal inhibition was observed at about 50 $\mu$g/ml. Two LNF III isomers, known as LNF I (Fuc$\alpha$1-2Gal$\beta$1-3GlcNAc$\beta$1-4Glc) and LNF II (Gal$\beta$1-3(Fuc$\alpha$1-4)GlcNAc$\beta$1-3Gal$\beta$1-4Glc), were also tested for inhibitory activity. The three LNF isomers are structurally closely related. They are composed of the same monosaccharides, but differ in the covalent linkages of these monosaccharides to form the pentassaccharide chain. Under the conditions of these experiments, neither LNF I (open squares) nor LNF II (closed circles) had inhibitory activity on cell adhesion (FIG. 6).

Although LNF III inhibited the interaction of activated platets and neutrophils, LNF III did not alter cell viability, as determined using the trypan blue exclusion method. In addition, a similar inhibitory effect of LNF III on platelet-HL60 cell and platelet-U937 cell interactions was demonstrated (data not shown).

To address the possibility of a nonspecific effect of LNF III on cell-cell interaction involving platelets, the effect of LNF III on ADP-induced platelet aggregation was examined. Platelet aggregation, which involves the binding of fibrinogen to glycoprotein IIb–IIIa, was equivalent in the presence or absence of LNF III. This example, in which cellular adhesion dependent upon glycoprotein IIb-IIIa was not affected by LNF III, suggests that LNF III specifically interferes PADGEM-mediated cell adhesion.

To extend this result, the effect of different concentration of LNF isomers on the binding of COS/PADGEM cells to HL60 cells was also studied. The results of a COS cell-PADGEM adhesion assay, in which the binding of $^{111}$In and bis-carboxyethyl-carboxyfluorescein-lableled HL60 cells to COS/PADGEM cells was monitored by assaying $^{111}$In activity (Example 2), are shown in FIG. 7. LNF III significantly inhibited the binding of radiolabeled HL60 cells to COS/PADGEM cells (closed square). In contrast, LNF I (open squares) did not inhibit this interaction and LNF II (closed circles) had only a small inhibitory effect. The inhibitory effect of LNF II was more apparent when the LNF to PADGEM ratio was high. These results suggest that PADGEM binds LNF III preferentially but may have some affinity for LNF II. It is possible that minor contamination of the LNF II preparation with LNF III can account for the inhibitory activity observed.

The inhibitory effects of LNF I, II, and III on the interaction of HL60 cells and COS/PADGEM was also studied morphologically in a blind assay. In these experiments, the binding of fluorescently labeled HL60 cells to COS/PADGEM cells was scored (Example 2). LNF III demonstrated significant inhibitory activity. In contrast, LNF I and LNF II demonstrated no inhibitory activity, and cell adhesion was comparable to assays in which LNF was absent. Mock-transfected COS cells did not bind HL60 cells.

The data demonstrate that LNF III specifically interferes with PADGEM-mediated cell—cell interactions. The inhibition of PADGEM-mediated cell—cell interactions by anti-CD15 monoclonal antibodies and CD15 antigen (e.g., LNF III), suggests that the PADGEM ligand on leukocytes shares structural features with CD15 positive cell surface structures (CD15 antigens), such as LNF III or Le$^x$, or a portion thereof.

Additional sugars were tested for inhibition of PADGEM- and ELAM-mediated interactions using the CHO-PADGEM and CHO-ELAM adhesion assay described in Example 2. The following sugars were tested at a single concentration:

3'-sialyllactose (i.e., NeuAc$\alpha$2-3Gal$\beta$1-4Glc);

6'-sialyllactose (i.e., NeuAc$\alpha$2-6Gal$\beta$1-4Glc);

3-fucosyllactose (i.e., Gal$\beta$1-4[Fuc$\alpha$1-3]Glc);

3'-sialyl-3-fucosyllactose (i.e., NeuAc$\alpha$2-3Gal$\beta$1-4[Fuc$\alpha$1-3]Glc).

3'-sialyllactose and 6'-sialyllactose were incubated with cells at a concentration of 0.5 mM, and 3-fucosyllactose and 3'sialyl-3-fucosyllactose were incubated with cells at a concentration of 0.25 mM. Under the conditions used, none of the four sugars tested appreciably inhibited PADGEM-mediated binding of HL60 cells to CHO-PADGEM transfectants. However, NeuAc$\alpha$2-3Gal$\beta$1-4[Fuc$\alpha$1-3]Glc decreased ELAM-mediated binding by 50–60%. The other three sugars behaved similarly in inhibition of ELAM-mediated binding, inhibiting adhesion by no more than 10% in any case under the conditions of the assay. Note that these experiments were done once only and at a single concentration in each case. It is possible that different conditions or higher concentrations may be needed to observe inhibition of PADGEM-mediated binding. Also, 3'-sialyllactose and 6'-sialyllactose lack an $\alpha$1,3-fucosyl residue typical of Le$^x$ core components.

Equivalents

Those skilled in the art will recognize or be able to ascertain, using no more than routine experimentation, many equivalents to the specific embodiments of the invention described herein. Such equivalents are intended to be encompassed within the scope of this invention.

We claim:

1. An in vitro method of inhibiting PADGEM-mediated or ELAM-1-mediated adhesion of leukocytes to cells selected from the group consisting of platelets and endothelial cells comprising contacting said cells with an effective amount of an inhibitor comprising a Le$^x$ core component under conditions whereby adhesion is inhibited.

2. The method of claim 1 wherein the inhibitor is a carbohydrate.

3. The method of claim 1 wherein the Le$^x$ core component is CD15 positive.

4. The method of claim 3 wherein the CD15 positive Le$^x$ core component is selected from the group consisting of: CD15 antigen, LNF-III and Le$^x$.

5. The method of claim 4 wherein the inhibitor is a carbohydrate.

6. The method of claim 5 wherein the carbohydrate is selected from the group consisting of: CD15 antigen, LNF-III, and Le$^x$.

7. An in vitro method of inhibiting the adhesion of a first cell bearing PADGEM with a second cell bearing a PADGEM ligand comprising contacting the first cell with and effective amount of an inhibitor comprising a Le$^x$ core component under conditions whereby cell adhesion is inhibited.

8. The method of claim 7 wherein the first cell is a platelet.

9. The method of claim 8 wherein the second cell is a leukocyte selected from the group consisting of: monocytes and neutrophils.

10. The method of claim 7 wherein the first cell is an endothelial cell.

11. The method of claim 10 wherein the second cell is a leukocyte selected from the group consisting of: monocytes and neutrophils.

12. The method of claim 7 wherein the inhibitor is a carbohydrate.

13. The method of claim 7 wherein the Le$^x$ core component is an α1,3 fucosylated lactosamine.

14. The method of claim 7 wherein the Le$^x$ core component is CD15 positive.

15. The method of claim 14 wherein the CD15 positive Le$^x$ core is selected from the group consisting of: CD15 antigen, a portion of CD15 antigen, LNF III, a portion of LNF III and Le$^x$.

16. The method of claim 7 wherein the inhibitor comprising a Le$^x$ core is selected from the group consisting of: a glycoprotein, a carbohydrate and a glycolipid.

17. An in vitro method of inhibiting the adhesion of PADGEM with a PADGEM ligand comprising contacting PADGEM with an effective amount of an inhibitor comprising a Le$^x$ core component under conditions whereby cell adhesion is inhibited.

* * * * *